US00PP37278P2

(12) United States Plant Patent
Romphoan

(10) Patent No.: US PP37,278 P2
(45) Date of Patent: Feb. 17, 2026

(54) ***EPIPREMNUM* PLANT NAMED 'ETH'**

(50) Latin Name: ***Epipremnum pinnatum* (L.) Engl.**
Varietal Denomination: ETH

(71) Applicant: CAMPO PARTICIPATIONS B.V., Nootdorp (NL)

(72) Inventor: Chayanisa Romphoan, Chiang Mai (TH)

(73) Assignee: Campo Participations BV, Nootdorp (NL)

( * ) Notice: Subject to any disclaimer, the term of this patent is extended or adjusted under 35 U.S.C. 154(b) by 0 days.

(21) Appl. No.: 19/316,641

(22) Filed: Sep. 2, 2025

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — James R. Holm; Plant Novelty Rights, LLC

(57) ABSTRACT

A new and distinct *Epipremnum* plant named 'ETH' particularly distinguished by its unique variegated leaf pattern and novel leaf fenestrations in the juvenile stage, vigorous growth habit, and ability to thrive under low light conditions.

3 Drawing Sheets

Figure 1:
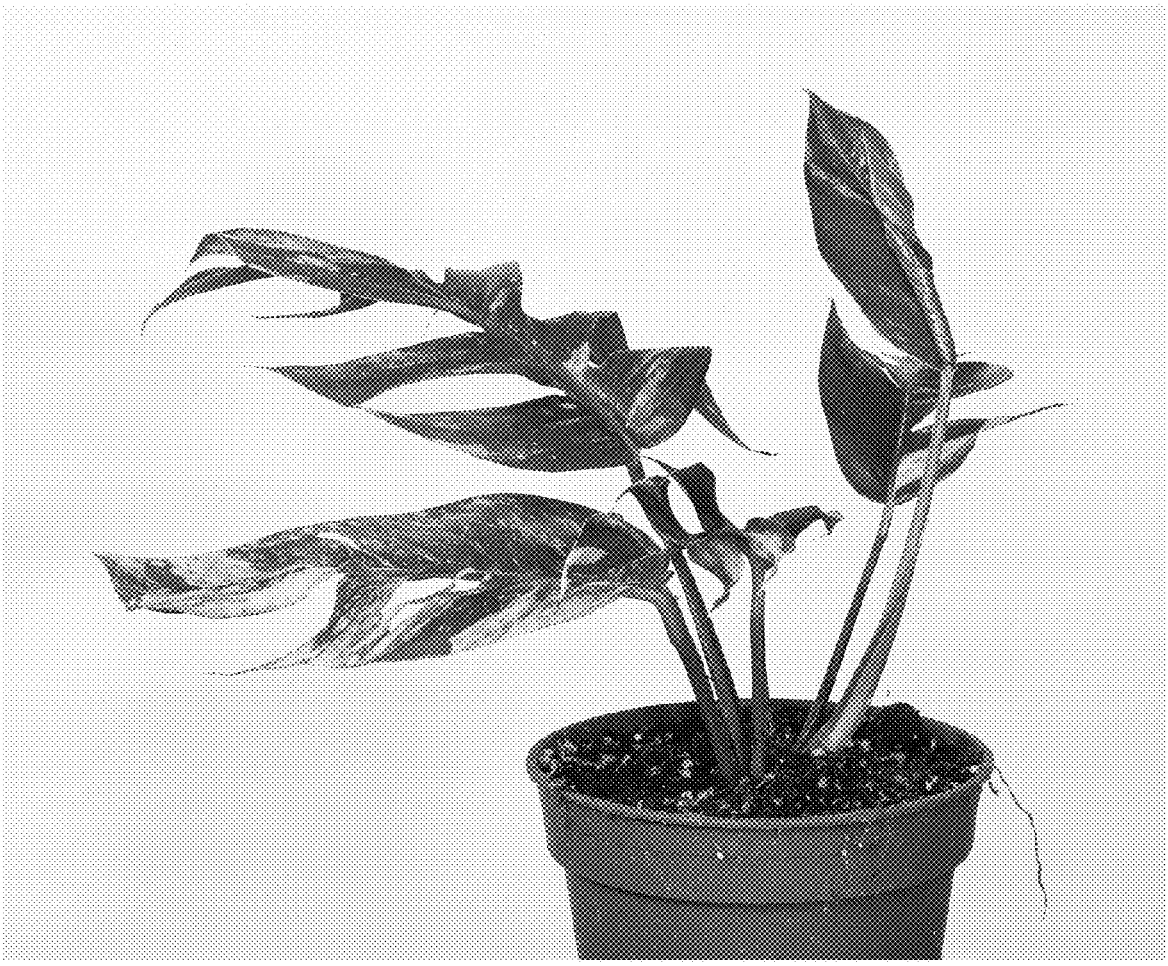

Genus and species: *Epipremnum pinnatum* (L.) Engl.
Variety denomination: 'ETH'.

BACKGROUND OF THE NEW PLANT

The present invention comprises a new and distinct variety of *Epipremnum* plant, botanically known as *Epipremnum pinnatum,* and hereinafter referred to by the variety name 'ETH'.

*Epipremnum pinnatum* is a heteroblastic tropical climbing vine, meaning the juvenile leaf forms differ from those of the adult form. In the juvenile stage, the leaf margins are observed to be entire. However, as the plant matures, leaves become larger and begin to develop fenestrations (incisions and perforations). Generally, under cultivated conditions and especially indoors, leaves of *E. pinnatum* will remain in the juvenile form indefinitely. *E. pinnatum* will transition to the adult form when provided a means for support to climb upwards beyond 1.5 to 3 meters off the ground. The exact transition point from the juvenile stage to the adult stage will vary depending on light, humidity, and nutrition. The development or discovery of an *E. pinnatum* cultivar with leaf fenestrations in the juvenile stage would be of high value in the commercial trade of *Epipremnum pinnatum* ornamental plants.

The new *Epipremnum* cultivar 'ETH' is a product of a planned breeding program located in Bangkok, Thailand. The objective of the breeding program was to select and reproduce *Epipremnum pinnatum* plants with unique leaf variegation, unique leaf shapes with fenestrations, and improved growing qualities. The new cultivar was discovered as a naturally occurring branch mutation in a population of unnamed and unpatented *Epipremnum pinnatum* plants growing in a conventional greenhouse in Bangkok, Thailand.

The new *Epipremnum* cultivar was selected based on its uniquely variegated leaf pattern and novel leaf fenestrations in the juvenile stage. 'ETH' was first reproduced asexually using vegetative meristem tip cuttings in May 2019 in Bangkok, Thailand. Asexual propagation by vegetative meristem tip cuttings of the new variety has shown that the unique features of the new variety are stable and reproduced true-to-type to date through twenty-one successive generations.

Plant Breeder's Rights for this variety have been applied for under CPVO application no. 20242069 on Sep. 3, 2024. 'ETH' has not been made publicly available or sold anywhere in the world more than one-year prior to the filing date of the present U.S. patent application.

SUMMARY OF THE INVENTION

The new *Epipremnum* cultivar 'ETH' has not been observed under all possible environmental conditions. The phenotype may vary somewhat with variations in environment such as temperature, day length, light intensity, water status, fertilizer rate and type, without, however, any variance in genotype. Leaves of 'ETH' can vary in shape from narrow ovate to broad ovate, while leaf margins may vary from entire to up to having 10 pinnatisect lobes. Newly emerged shoots from cuttings with entire leaf margins may emerge with or without fenestrations, while newly emerged shoots from cuttings with partly pinnatisect or pinnatisect leaves may emerge with entire leaf margins or with some fenestrations. Leaf variegation varies from almost non-variegated to leaves with strong variegation.

The following are the most outstanding and distinguishing characteristics of this new *Epipremnum* cultivar. The combination of these characteristics distinguishes 'ETH' as a new and distinct variety of *Epipremnum.*

1. Unique variegated leaf pattern and novel leaf fenestrations in the juvenile stage;
2. Vigorous growth habit; and
3. Ability to thrive under low light conditions.

The new *Epipremnum* cultivar can be distinguished from plants of its progenitor or parent *Epipremnum pinnatum* by having larger leaves with up to 10 pinnatisect lobes, whereas the parent or progenitor plants have smaller leaves with no pinnatisect lobes.

The new *Epipremnum* cultivar can be distinguished from the related known variety of *Epipremnum* cultivar 'Albo Variegata' (unpatented) in the following characteristics:

1. 'ETH' has a more compact, bushy and rounded plant habit with shorter internodes, whereas 'Albo Variegata' has a taller and vining plant habit with longer internodes and requires artificial support for its growth.
2. 'ETH' has medium sized leaves which are generally smaller and broader, whereas 'Albo Variegata' has larger and elongated shaped leaves with narrower fenestrations and is more suited for climbing growth.
3. 'ETH' has leaves that are broader and more deeply lobed with multiple fenestrations, whereas 'Albo Variegata' has moderately lobed leaves with narrower fenestrations as well as having leaf segments that are more elongated.
4. 'ETH' has a base leaf color that is brighter green, whereas 'Albo Variegata' has a base leaf color that is darker green.
5. 'ETH' has a mottled and marbled leaf variegation pattern that is a distinct yellow, evenly distributed across the entire leaf surface and is stable and consistent, whereas 'Albo Variegata' has a leaf variegation pattern that is creamy-white to light green and is generally separated into segments or patches rather than marbled.
6. 'ETH' has petioles that are shorter contributing to its more compact plant form, whereas 'Albo Variegata' has petioles that are longer contributing to its more open plant form.

DESCRIPTION OF THE PHOTOGRAPHS

This new *Epipremnum* cultivar is illustrated by the accompanying-colored photographs which show the overall appearance and distinct characteristics of the plant. The colors shown are as true as can be reasonably obtained by conventional photographic procedures. The photographs are of a 24-week-old plant grown in a 17-centimeter circular container in a conventional glass greenhouse in Naaldwijk, The Netherlands. Colors in the photographs may differ slightly from the color values cited in the botanical description which accurately describes the colors of the new variety.

Figure 2:
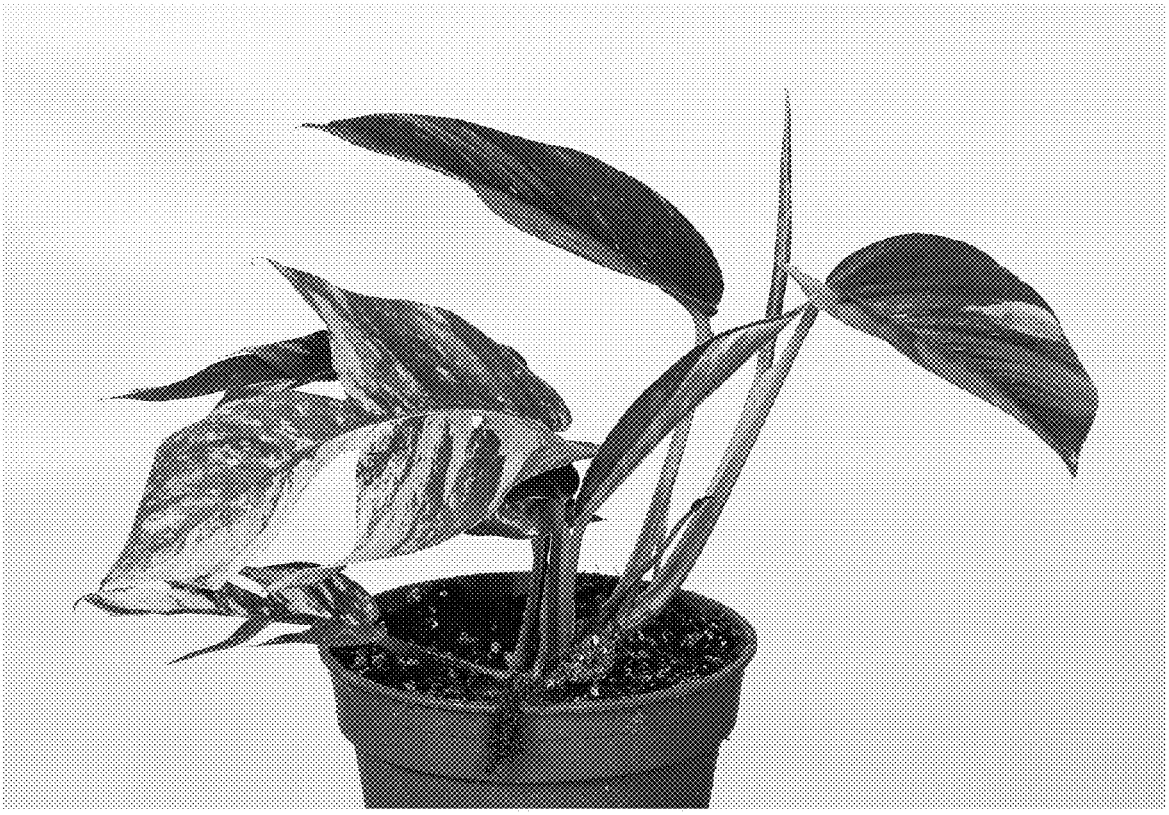
Figure 3:
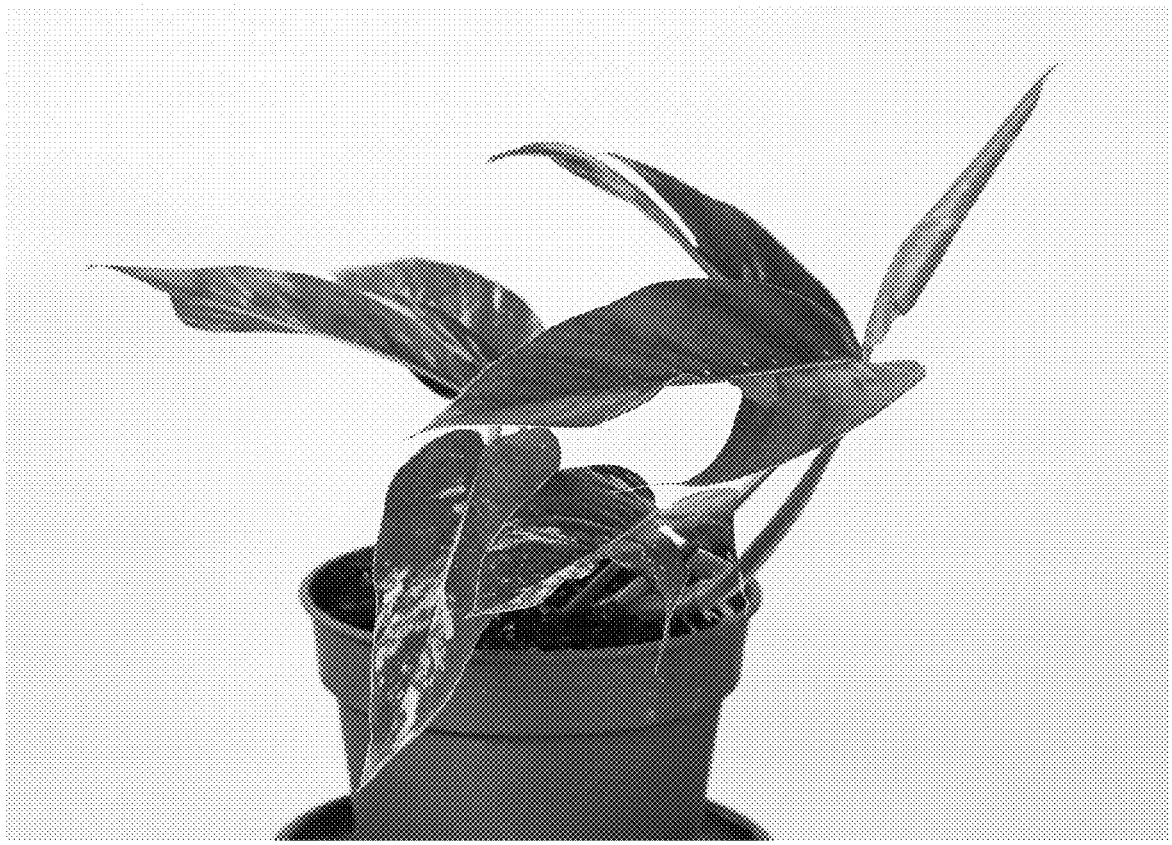

FIGS. 1, 2 and 3 shows the overall plant form and foliage of typical plants of the new *Epipremnum* cultivar 'ETH'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a conventional greenhouse located in Naaldwijk, The Netherlands. Plants were grown under normal daytime light levels in Naaldwijk, The Netherlands with no supplemental lighting. Detailed descriptions were taken in August 2024 from 24-week-old plants grown in 17-centimeter circular containers. Measurements and numerical values represent averages of typical plant types.

DETAILED BOTANICAL DESCRIPTION

Classification:

*Family*.—Araceae.

*Botanical*.—*Epipremnum pinnatum* (L.) Engl.

*Common*.—Pothos.

*Denomination*.—'ETH'.

General Description:

*Plant type*.—Tropical perennial vine.

*Approximate container size and/or cropping system*.—13.0 cm or larger pots.

*Growth habit*.—Broad, with spreading upright growth.

*Overall plant shape*.—Flattened, globular.

*Height from soil level to top of foliar plane*.—27.8 cm.

*Plant spread*.—33.0 cm.

*Growth rate*.—Moderate.

*Plant vigor*.—Moderate.

*Branching habit*.—Basal branching with no lateral branches present.

*Propagation type*.—Vegetative meristem tip cuttings.

Branch description:

*Number of main branches or stems per plant*.—1.

*Main stem length*.—Average 6.2 cm.

*Main stem diameter*.—Average 1.0 cm.

*Main stem internode length*.—Average 3.5 cm.

*Stem appearance and shape*.—Rounded to slightly flattened, shallow axially ribbed and slightly rugose.

*Stem luster*.—Glossy.

*Stem aspect/angle from vertical*.—Average 40°, varying between 20° and 60° to horizontal.

*Stem strength*.—Strong.

*Stem color*.—Developing stems: Near 143A and 143B (green) and axillary striped near 154B and 154C (yellow-green). Mature stems: Near 143C (green) and axillary striped near 151C and 151D (yellow-green). Internodes: Near 143C (green) and axillary striped near 151C and 151D (yellow-green).

*Pubescence*.—Not present.

Foliage description:

*Leaf type*.—Simple.

*Leaf arrangement*.—Alternate.

*Number of leaves per stem*.—Average of 5.

*Lamina*.—Shape: Narrow ovate to broad ovate. Length: Average 21.0 cm. Width: Average 11.6 cm. Aspect: Slightly carinate. Apex shape: Apiculate. Base shape: Truncate to cordate. Margins: Entire to pinnatisect, varying from no incisions to 10 incisions. Margin undulation: Slightly to moderately coarsely undulate. Lobation: Varying from unlobed to 10 lobes. Depth of sinuses: Deep. Sinus orientation: Parallel to divergent. Texture (both upper and lower surfaces): Smooth, glabrous. Pubescence: Not present. Luster (both upper and lower surfaces): Moderately glossy to glossy. Color: Juvenile foliage: Upper surface: Closest to NN137A (green); irregularly blotched and marbled with near 150A and 151D (yellow green). Lower surface: Near 146A (yellow green); irregularly blotched and marbled with near 150A (yellow green). Mature foliage: Upper surface: Near 137A, NN137A, and NN137B (green); irregularly blotched and marbled with near 150A to 150D (yellow green) and 10C and 10D (yellow). Lower surface: 144A and a blend of 144A and 146B (yellow green); irregularly blotched and marbled with near 150A to 150D (yellow green) and 10D (yellow). Venation: Pattern: Pinnate. Color (mature leaves): Upper surface: Near 137A, NN137A, and NN137B (green); irregularly axially striped with near 150A to 150D (yellow green). Lower surface: Near 144C (yellow green).

*Petiole*.—Length: Average 12.7 cm, including geniculum. Diameter: Flattened on the upper side, average 0.6 cm, horizontal and vertical. Texture (both upper and lower surfaces): Smooth, glabrous. Luster (both upper and lower surfaces): Slightly glossy. Strength: Medium. Color: Upper surface: Near 143B (green); slightly axially striped with near N144B (yellow-green). Lower surface: Near 143A (green); slightly axially striped with near 144B and 144C (yellow-green).

*Geniculum*.—Length: Average 2.1 cm. Diameter: Average 0.7 cm. Aspect: Rounded, upper side slightly flattened. Color: Upper surface: Near 143B (green). Lower surface: Near 144A and 144B (yellow-green).

*Petiole wings*.—Length: Average 12.0 cm. Width: Average 0.7 cm. Color: A blend of near 145C and 145D (yellow-green); axially veined near 143B and 143C (green); on mature leaves, the wings dry and become near N199A and N199B (greyed-brown).

Inflorescence: None observed to date.

Heat tolerance: At least tolerant to temperatures up to 40 degrees Celsius.

Cold tolerance: At least hardy to USDA zone 10.

USDA hardiness zones: Zones 10 to 13.

Rain tolerance: Moderate to high.

Wind tolerance: Low to Moderate.

Disease and pest tolerance: No claims are made to any superior disease or insect resistance or tolerance.

What is claimed is:

1. A new and distinct cultivar of *Epipremnum* plant named 'ETH', substantially as illustrated and described herein.

* * * * *